United States Patent
Perriello

(12) 
(10) Patent No.: US 6,918,354 B2
(45) Date of Patent: Jul. 19, 2005

(54) METHOD AND APPARATUS FOR BUTANE-ENHANCED AQUATIC PLANT AND ANIMAL GROWTH

(75) Inventor: Felix Anthony Perriello, Norwood, MA (US)

(73) Assignee: Global BioSciences, Inc., North Attleborough, MA (US)

( * ) Notice: Subject to any disclaimer, the term of this patent is extended or adjusted under 35 U.S.C. 154(b) by 0 days.

(21) Appl. No.: 10/324,256

(22) Filed: Dec. 19, 2002

(65) Prior Publication Data

US 2003/0167686 A1 Sep. 11, 2003

Related U.S. Application Data

(63) Continuation-in-part of application No. 10/282,891, filed on Oct. 29, 2002.
(60) Provisional application No. 60/343,042, filed on Dec. 20, 2001.

(51) Int. Cl.[7] .......................... A01K 61/02; A01G 7/00; A01G 33/00
(52) U.S. Cl. ...................................... 119/231; 47/58.1 R
(58) Field of Search ................................ 119/231, 268; 119/263; 47/58.1 R, 1.4

(56) References Cited

U.S. PATENT DOCUMENTS

| | | | |
|---|---|---|---|
| 3,183,171 A | 5/1965 | Schreiner | |
| 3,184,891 A | 5/1965 | Frantzen | |
| 3,185,117 A | 5/1965 | Frantzen | |
| 3,361,555 A | 1/1968 | Herschler | |
| 3,372,658 A | * 3/1968 | Ammann | 111/119 |
| 3,474,001 A | 10/1969 | Leavitt | |
| 3,550,319 A | 12/1970 | Gaines, Jr. | |
| 3,661,549 A | 5/1972 | Freytag et al. | |
| 3,813,290 A | 5/1974 | Heilweil et al. | |

(Continued)

FOREIGN PATENT DOCUMENTS

| | | | | |
|---|---|---|---|---|
| JP | 7-50955 | * | 2/1995 | .......... A01K/63/02 |
| JP | 10306003 A | * | 11/1998 | .......... A01N/43/16 |
| WO | WO 3037066 A2 | | 5/2003 | |
| WO | WO 03/053143 A2 | * | 7/2003 | |

OTHER PUBLICATIONS

Schmidt et al. 2004. Gas hydrates and methane plumes at Hydrate Ridge. 13 pages.*

Anonymous. undated. Lost City Expedition. at http://www.lostcity.washington.edu/science/instruments/.*

Cary et al. 1988. Mussel growth supported by methane as sole carbon and energy source. Science 240: 78–80.*

Toccalino et al., "Nitrogen Limitation and Nitrogen Fixation during Alkane Biodegradation in a Sandy Soil," *Applied and Environmental Microbiology*, Sep. 1993; p. 2977–2983, vol. 59, No. 9.

N. Hamamura et al., "Diversity in Butane Monooxygenases Among Butane–Grown Bacteria," *Applied and Environmental Microbiology*, vol. 65, No. 10, Oct. 1999, pp. 4586–4593.

*Primary Examiner*—Jeffrey L. Gellner
(74) *Attorney, Agent, or Firm*—Alan G Towner, Esq.; Robert P. Lenart, Esq.; Pietragallo, Bosick & Gordon

(57) ABSTRACT

A method of enhancing aquatic organism growth is provided. The method comprises the step of introducing an alkane into water containing the organism. The alkane can be introduced intermittently, either alone or with another gas such as oxygen. Nutrients can be introduced with the alkane or separately. The alkane can comprise a butane substrate and can include at least one of n-butane and iso-butane. The organism can be selected from the group of: fish, crustaceans, mollusks, algae and aquatic plants. Organisms grown by the method and systems for practicing the method are also included.

39 Claims, 6 Drawing Sheets

U.S. PATENT DOCUMENTS

| | | |
|---|---|---|
| 4,119,429 A | 10/1978 | Lovness |
| 4,321,142 A | 3/1982 | Starr |
| RE31,924 E | 6/1985 | Starr |
| 4,713,343 A | 12/1987 | Wilson, Jr. et al. |
| 5,147,441 A | 9/1992 | Megeed |
| 5,266,096 A | 11/1993 | Slavensky |
| 5,441,885 A | 8/1995 | Goldberg et al. |
| 5,697,186 A | 12/1997 | Neyra et al. |
| 5,733,355 A | 3/1998 | Hibino et al. |
| 5,802,996 A | 9/1998 | Baxter |
| 5,888,396 A | 3/1999 | Perriello |
| 5,951,978 A | 9/1999 | Red'kina |
| 6,105,309 A | 8/2000 | Takayanagi |
| 6,110,372 A | 8/2000 | Perriello |
| 6,156,203 A | 12/2000 | Anthony |
| 6,194,193 B1 | 2/2001 | Drahos et al. |
| 6,210,579 B1 | 4/2001 | Perriello |
| 6,244,346 B1 | 6/2001 | Perriello |
| 6,245,235 B1 | 6/2001 | Perriello |
| 6,474,264 B1 * | 11/2002 | Grimberg et al. ........... 119/231 |
| 6,488,850 B2 | 12/2002 | Perriello |
| 2003/0041515 A1 | 3/2003 | Layzell et al. |
| 2003/0084609 A1 | 5/2003 | Perriello et al. |
| 2003/0167686 A1 | 9/2003 | Perriello |
| 2003/0201227 A1 * | 10/2003 | Perriello ..................... 210/610 |

* cited by examiner

METHOD AND APPARATUS FOR BUTANE-ENHANCED AQUATIC PLANT AND ANIMAL GROWTH

CROSS-REFERENCE TO RELATED APPLICATION

This application is a Continuation-in-part of U.S. patent application, Ser. No. 10/282,891, filed Oct. 29, 2002, the disclosure of which is hereby incorporated by reference, and claims the benefit of U.S. Provisional Patent Application Ser. No. 60/343,042, filed Dec. 20, 2001.

FIELD OF THE INVENTION

The present invention provides enhanced growth of aquatic plants and animals. More particularly, the invention provides methods and apparatus for using alkanes, such as butane, in order to stimulate aquatic plants and animal growth.

BACKGROUND INFORMATION

Only in unique environmental situations do species of organisms live entirely alone. Communities almost always have mixed populations. Due to this variety, many types of interactions, some beneficial, others not, are possible due to the members of an ecosystem's (fresh water or salt-water) community. Symbiosis, the intimate living together of two or more kinds of plants and/or organisms in a mutually beneficial environment has played a key role in the evolution of many species.

In natural environments, many types of symbiosis are easily discernible, for example, the rhinoceros and parasite feeding birds, the shark and the pilot fish. Aphids suck phloem, removing certain amino acids, sugars and other nutrients from it while excreting most of it as honeydew or sugar-lerp, where it is harvested by the Aborigines in Australia. Some species of aphids have been domesticated by several species of ants. These aphids do not excrete their honeydew continuously, but only in response to caressing movements of the ant's antennae and forelimbs. The aphids involved in this symbiotic relationship with the ants have lost all of their own natural defenses, including their hard outer skeletons. The aphids rely entirely on their hosts for protection. In other cases, the relationship is not readily apparent, such as the leaf-cutter ants and bacteria that produce antibiotics that increase the survivability of the ant host.

Commercial fish harvesters use a variety of amendments to enhance fish growth. Some include vitamins and other nutrients to maintain good health and to help fish resist diseases. Other methods include genetic alteration and manipulation.

SUMMARY OF THE INVENTION

This invention provides a method of enhancing aquatic organism growth comprising the step of introducing an alkane into water containing the organism. The alkane can be introduced intermittently, either alone or with another gas such as oxygen. Nutrients can be introduced with the alkane or separately. The alkane can comprise a butane substrate and can include at least one of n-butane and iso-butane.

The organism can be selected from the group of: fish, crustaceans, mollusks, algae and aquatic plants.

The invention also encompasses organisms grown by the above method.

The invention further encompasses a system for enhancing aquatic organism growth comprising means for introducing an alkane into water containing the organism. The alkane can be introduced intermittently, either alone or with another gas such as oxygen. Nutrients can be introduced with the alkane or separately. The alkane can comprise a butane substrate and can include at least one of n-butane and iso-butane.

The means for introducing an alkane can comprise at least one injector in flow communication with an alkane source, wherein at least a portion of the injector is positioned in the water. The alkane source can comprise a butane cylinder in flow communication with a source of pusher gas. The butane substrate can be supplied to the injector in gaseous or liquid form.

DETAILED DESCRIPTION

Figure 1:
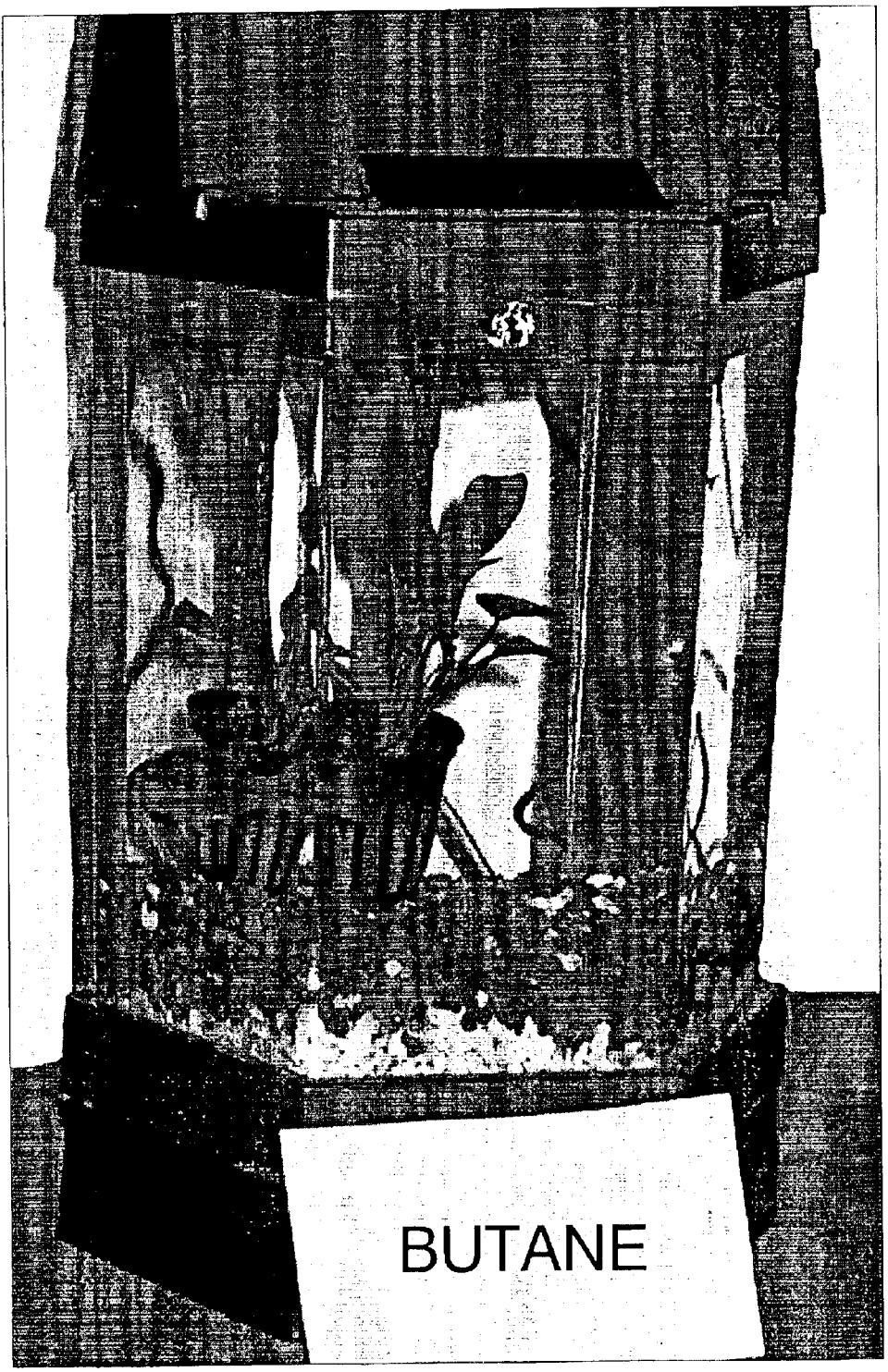
FIG. 1 is a pictorial representation of an experimental tank setup for butane-enhanced fish growth.

Butane can be used to enhance the growth of a wide variety of plant and animal organisms in aqueous environments such as fresh water and salt-water environments. By enhancing the entire ecosystem, organisms in a symbiotic relationship directly accrue the benefits of the enhancement. Thus, butane enhances the microbial populations in an ecosystem, such as fungi, algae, phytoplankton, zooplankton, and protists, as well as other microscopic and macroscopic organisms. Butane may stimulate the growth of organisms at the bottom of the food chain, creating a chain reaction of increased food source and opportunity for growth in numbers throughout the food chain. The addition of butane may turn a fresh water or salt water environment into a nutrient-rich soup. This is especially important for filter-feeders such as mollusks and the like.

The controlled addition of butane to an aquatic environment may also lead to an increase in growth of algae and aquatic plants which serve as a cover and protection for young fish (fry) and may lead to increased survivability of fry and smaller fish.

Fish thriving in this environment receive the benefit of the enhanced populations. For example, algae release oxygen in fresh or salt water. Butane enhancement stimulates the growth of algae. This oxygenation is directly beneficial to fish and other fresh water and salt water organisms.

Many types of bacteria colonize fish scales and gills. These bacteria play a role in the maintenance of good health. If the microbial population is disturbed, or pathogenic microorganisms take hold, the overall health of the fish is jeopardized. Butane may stimulate a variety of helpful organisms while showing no harmful effects to the ecosystem tested.

In low doses, butane may have an effect on fish which stimulates an increase in appetite. The increase in appetite also results in a larger consumption of food and, consequently, faster and larger growth. Enhanced fish growth through butane biostimulation may become an acceptable alternative to genetic alteration.

Larger and meatier fish, grown and harvested inexpensively, could be used to combat worldwide hunger and improve the welfare of human society.

In a freshwater environment, butane stimulation may enhance symbiotic relationships by enhancing the growth of organisms such as algae, plants such as angiosperms, cattails, rushes, water lilies, duckweed and a variety of other aquatic plants, snails, bacteria, fungi, arthropods, insects, clams, worms, fish, frogs, salamanders, turtles, mollusks, amphibians, protists, protozoa, small fresh water crustaceans such as daphnia and cyclops, prokaryotes, phytoplankton, zooplankton, as well as a variety of other microscopic and macroscopic organisms.

In a salt water environment, butane stimulation may enhance symbiotic relationships by enhancing the growth of organisms such as algae, aquatic plants, snails, bacteria, fungi, arthropods, insects, clams, worms, fish, turtles, mollusks, protists, protozoa, small salt water crustaceans, prokaryotes, phytoplankton, zooplankton, starfish, crustaceans, sponges, sea anemones, as well as a variety of other microscopic and macroscopic organisms.

Alkane enrichment, preferably butane, will increase the indigenous microscopic and macroscopic populations in aqueous environments such as fresh and/or salt water environments. The alkane may include methane, ethane, and propane with butane (including n-butane and iso-butane) being the preferred choice. This natural increase at the expense of butane results in increased microscopic and macroscopic populations that may serve direct and obvious benefits, for example, to fish populations, such as increased nutrient uptake, faster overall growth, resistance to disease and stress such as temperature change.

In one embodiment, butane, as a highly soluble gas substrate, may be used to effectively stimulate fish ponds, tanks, farms, lagoons or any aquatic system. Butane is non-toxic. It may also be used to effectively enhance the growth of fish, crustaceans, mollusks and the like. Butane may also enhance the growth of gems formed by bivalve mollusks such as pearls. The following lists provide examples of some organisms that may be treated in accordance with the present invention.

For example, the present invention is applicable for the growth enhancement or treatment of the following types of fish: (1) Cartilage fishes (Class Chondrichthyes); and (2) bony fishes (Class Osteichthyes). Both classes are of the phylum Chordata.

The Chondrichthyes: sharks, frilled sharks, Sixgill and Sevengill Cow-sharks, Sand sharks, Goblin sharks, Mackerel sharks, Thresher sharks, Basking sharks, Whale sharks, Carpet and Nurse sharks, Catsharks, False Catsharks, Smooth Dogfishes, Requiem sharks, Hammerhead Sharks, Hornsharks, Saw Sharks, Spiny Dogfishes, Spineless Dogfishes, Alligator Dogfish, Angel Shark, Skates and Rays, Electric Rays, Guitarfishes, Sawfishes, Skates, Stingrays, Whiprays, Butterfly Rays, Round Rays, Eagle Rays, Bat Rays, Cow-Nosed Rays, Devil Rays, Chimaeroids, Short-Nosed Chimaeras or Ratfishes, Long-Nosed Chimaeras, and Plow-Nosed or Elephant Chimaeras.

The Osteichthyes: Bichirs, Sturgeons, Paddlesfishes, Bowfin, Gars, Tarpon, Bonefish or Ladyfish, Slickhead Fishes, Herring, Sardines, Gizzard Shad, Round Herring, Wolf Herring, Anchovy, Milkfish, Salmon, Trout, Whitefishes, Grayling, Smelts, Capelin, Galaxiids, Brisstlemouths, Hatchet Fishes, Viper Fishes, Bony Tongues, Butterfly Fish, Mooneye, Featherbacks, Mormyrids, Beaked Salmon, Pike, Pickerel, Muskellunge, Mud Minnows, Blackfish, Iniomous Fishes, Lizard Fishes, Thread-Sail Fishes, Greeneyes, Grid-Eye Fishes, Spider Fishes, Lantern Fishes, Bombay Duck, Barracudinas, Pearleyes, Saber-Tooth Fishes, Lancet Fishes, Hammerjaw, Javelin Fish, Deep-Sea Giganturid Fishes, Deep-Sea Gulper Eels, Characid and Piranha, Electric Eel and Knifefishes, Bitterling, Carp and Minnows, Suckers, Loaches, Gyrinocheilids, Hillstream Fishes, Catfishes, Doradid Catfishes, Callichthyid Catfishes, Plecostomus, Banjo Catfishes, Ariid Marine Catfishes, Plotosid Marine Catfishes, Clariid Catfishes, Silurid Catfishes, Pimelodid Catfishes, Bagrid Catfishes, Parasitic Catfishes, North American Catfishes, Schilbeid Catfishes, Upside-Down Catfishes, Electric Catfish, Eels, Fresh Water Eels, Parasitic Snubnosed Eel, Moray Eels, Snake Eels, Snipe Eels, Deep-Sea Eels, Conger Eels, Worm Eels, Deep-Sea Spiny Eels, Needlefishes, Halfbeaks, Sauries, Flying Fishes, Blind Fish, Egg-Laying Topminnows, Viviparous Topminnows, Goodeids, Four-Eyed Fishes, Jenynsiids, Andrianichthyids, Troutperch, Pirateperch, Tube-Mouthed Fishes, Pipefishes, Seahorses, Ghost Pipefishes, Indostomids, Shrimpfishes, Snipefishes, Cometfish, Trumpetfishes, Codfishes, Hake, Deep-Sea Rattails or Grenadiers, Opah, Squirrelfishes, Alfonsinos, Lantern-Eye Fishes, Barbudos, Pinecone Fishes, Gibber, Prickle, Bigscale and Whalefishes, John Dories, Boarfishes, Grammicolepids, Perchlike Fishes, Bass and Groupers, Tigerfishes, Aholeholes, Sunfishes, Catalufas or Bigeyes, Cardinal Fishes, Perches, Darters and Walleyes, Redfish, Blanquillos, Bluefish, Cobia, Carangids, Cavallas, Jacks, Pompanos and Scad, Dolphins, Robalos, Snook and Glassfish, Snappers, Nemipterids, Tripletails, Slipmouths, Mojarras, Grunts, Croakers, Goatfishes, Lethrinids, Porgies and Sea Breams, Fingerfishes, Archerfishes, Rudderfishes, Nibblers, Batfishes, Spadefishes, Scats, Angelfishes and Butterfly Fishes, Leaf Fishes and Nandids, Cichlids, Hawkfishes, Surfperches, Damselfishes, Wrasses, Parrotfishes, Sandfishes, Jawfishes, Weeverfishes, Sand Divers, Sand Lances, Electric Stargazers, Sand Stargazers, Ice Fishes, Moorish Idol, Surgeonfishes, Rabbitfishes, Cutlass Fishes and Hairtails, Deep-Sea Snake Mackerels or Escolars, Mackerels, Tunas, Billfishes (including Marlins, Sailfishes, and Spearfishes), Swordfish, Louvar, Sleepers, Gobies, Eel Gobies, Loach Goby, Dragonets, Blennies, Scaled Blennies or Klipfishes, Pricklebacks, Gunnels, Wolf Fishes and Wolf Eels, Eelpouts, Brotulids, Cusk Eels, Cucumber and Pearl Fishes, Butterfishes, Labyrinth Fishes, Snakeheads, Barracuda, Silversides, Mullets, Phallostethids, Threadfins, Scorpionfishes and Rockfishes, Sea Robins, Armored Sea Robins, Sculpins, Grunt Sculpin, Sea Poachers and Alligator Fishes, Snailfishes, Lumpsuckers, Gumards, Sticklebacks and Tubenose, Tubenose, Sea Moths, Flatfishes, Left-Eyed Flounders, Right-Eyed Flounders, Soles, Tongue Soles, Remoras or Suckerfishes, Triggerfishes, Puffers, Sharp-Nosed Puffers, Porcupine Fishes and Burnfishes, Trunkfishes, Ocean Sunfishes, Ragfishes, Clingfishes, Toadfishes and Midshipmen, Anglerfishes, Goosefishes or Monkfishes, Frogfishes, Batfishes, Deep-Sea Anglers, Spiny Eels, Swamp Eels, Coelacanths, and Lungfishes.

The present invention is also applicable to enhancing the growth of crustaceans, comprising the class Crustacea, phylum Arthropoda. Principal classes include crabs such as King Crab, Dungeness Crab, Rock Crab, Tanner Crab and Kona Crab. Other crustaceans include lobsters such as the American Lobster, the European Lobster and Norwegian Lobster, shrimp (over 2000 known species), crawfish, Caryfish and Antarctic Krill.

The present invention is further applicable to enhancing the growth of mollusks, comprising the phylum Mollusca. Principal classes include the bivalves or clams such as the Soft shell clams, Surf clams, American quahog, Razor clam, Ocean quahog, Common edible cockle and Devon cockle. Mussels include the Mediterranean mussel, Blue mussel, California mussel, Asian mussel, Philippine mussel, Indian mussel, New Zealand mussel and Brazilian mussel. Scallops include the American scallop, Pilgrim's scallop and Giant scallop. Oysters include the Pearl oyster, Common European oyster, Japanese oyster, Portuguese oyster, American oyster and Chilean oyster. Enhanced oyster growth may result in enhanced pearl size. Gastropods include Abalone, Giant conch, Queen conch, Crown conch, Louisiana conch, Escargot snail. Cephalopods include the Common squid, North American common squid, North European squid, Opalescent squid, Giant squid, Short-finned squid, Common octopus and Common cuttlefish.

The present invention is also applicable to enhancing the growth of tropical fish, phytoplankton and zooplankton, algae, including green, bluegreen, red and brown algae, insects, arthropods, worms, frogs, salamanders, turtles and amphibians.

The present invention also enhances aquatic plant growth. Enhancing aquatic plant growth may have implications for the following industries: oxygen production, cosmetics, drugs and pharmaceuticals, lubricants, food for human and animal consumption, food preparation, bacteriology, mycology, stabilizer for emulsions, shoe polish, filters/rubbing compounds (polish), thickening agents, suspending/stabilizing agents, floor polish, pest control, insect control, diatomaceous earth production, tanning industry, agriculture, rubber manufacture, shaving creams, alginic acids, latex manufacture, ice cream, agar, nutrients, sewage treatment, fertilizers, soil amendments, semi-conductor, industrial supplies, soaps and laundry/janitorial supplies, jewelry and watches, durable goods, drugs and proprietaries, frozen foods, dairy products, poultry and its products, confectionary, fish and seafoods, meat and meat products, fresh fruits and vegetables, grain, livestock, chemicals and allied products, fuel, performance enhancer for petroleum products, beer and ales, wines and distilled beverages, farm supplies, tobacco and its products, paints, varnishes and supplies, cold temperature storage, liquefied petroleum storage, fuel oil storage and distribution, power production facilities, dry cleaning facilities, insulation, insulation for equipment, insulation for extreme environments, industrial launderers, photographic studios, commercial photography, disinfecting and exterminating, research and development laboratories, photo finishing labs, commercial testing labs, auto repair services and garages, car washes, automotive services, refrigeration and air conditioning services and repair, amusement and recreation services, health services, medical and/or dental laboratories, fabric finishing plants, textile manufacture and industries, cordage and twine, lumber and wood industries, paper and allied products, pulp mills, boxes and cans, printing and publishing, electroplating, petroleum and coal products, rubber and plastics, leather and leather products, stone, clay and glass products, primary metal industries, smelting and refining, steel, aluminum, electrometallurgical, foundry, fabricated metal products, plating and polishing, ordnance and accessories, valves and fittings, forgings, screw machines products, non-electrical machinery, pumps and pumping equipment, transformers, construction machinery, internal combustion engines, motors and generators, carbon and graphite products, industrial controls, welding apparatus, batteries and battery storage, motor vehicles, truck and bus, aircraft, aircraft engines and engine parts, aircraft equipment, railroad equipment, guided missiles, guided missiles and space vehicles, propulsion units, automatic temperature controls, fluid meters and counting devices, instruments for measuring electricity, measuring and controlling devices, surgical and medical instruments, silverware and plated ware, welding and cutting industries.

Butane also stimulates the growth of fungi (Kingdom Fungus), protists (Kingdom Protista) and prokaryotes (Kingdom Prokaryota). Bacteria may include the following Groups (in addition to fungi, algae, protozoa, rotifers and other aerobic and anaerobic microbial populations):

Group 1: The Spirochetes

Group 2: Aerobic/Microaerophilic, motile, helical/vibroid, gram-negative bacteria Group 3: Nonmotile (or rarely motile), gram-negative bacteria Group 4: Gram-negative aerobic/microaerophilic rods and cocci Group 5: Facultatively anaerobic gram-negative rods Group 6: Gram-negative, anaerobic, straight, curved, and helical bacteria Group 7: Dissimilatory sulfate- or sulfur-reducing bacteria Group 8: Anaerobic gram-negative cocci Group 9: Anoxygenic phototrophic bacteria Group 10: Oxygenic phototrophic bacteria Group 11: Aerobic chemolithotrophic bacteria and associated organisms Group 12: Budding and/or appendaged bacteria Group 13: Sheathed bacteria Group 14: Nonphotosynthetic, nonfruiting gliding bacteria Group 15: The fruiting, gliding bacteria and the Myxobacteria Group 16: Gram-positive cocci Group 17: Endospore-forming gram-positive rods and cocci Group 18: Regular, nonsporing, gram-positive rods Group 19: Irregular, nonsporing, gram-positive rods Group 20: The mycobacteria Groups 21–28: The actinomycetes Group 21: Nocardioform actinomycetes Group 22: Genera with multiocular sporangia Group 23: Actinoplanetes Group 24: Streptomycetes and related genera Group 25: Maduromycetes Group 26: Thermomonospora and related genera Group 27: Thermoactinomycetes Group 28: Genus Glycomyces, Genus Kitasatospira and Genus Saccharothrix Group 29: The Mycoplasmas—cell wall-less bacteria Group 30: The Methanogens Group 31: Archaeal sulfate reducers Group 32: Extremely halophilic, archaeobacteria (halobacteria)

Group 33: Cell wall-less archaeobacteria

Group 34: Extremely thermophilic and hyperthermophilic SO-metabolizers

Facultative anaerobes and microaerophilics are bacteria capable of surviving at low levels of oxygen. They do not require strict anaerobic conditions such as the obligate anaerobes. They include acidophilic, alkaliphilic, anaerobe, anoxygenic, autotrophic, chemolithotrophic, chemoorganotroph, chemotroph, halophilic, methanogenic, neutrophilic, phototroph, saprophytic, thermoacidophilic and thermophilic.

EXAMPLE 1

On Day No. 1 five acrylic hexagonal aquariums equipped with air filters and bed purification media (gravel only—no carbon), 5 watt fluorescent light bulbs and thermometers were prepared with 1.66 gallons of spring water and two inches of gravel, as shown in FIG. 1. One plant (Anuba Congensis) was placed in each tank. The tanks were labeled Control 1, Control 2, Butane 1, Butane 2 and Butane 3. The Butane tanks were prepared with removable tygon injection tubes (35 cm. length) each connected at one end to an air delivery stone/sponge (submerged to tank bottom during injection) and at the other end to a syringe port equipped with a Teflon coated septum. Six large mouth bass, purchased from Carolina Biological Supply, were each placed in a tank (two of the smaller fish placed together in Butane 2 to see effects of stress). The lengths of the bass were measured with a ruler. The lengths were recorded as follows:

Control 1—6.0 cm

Control 2—7.5 cm

Butane 1—7.5 cm

Butane 2a—6.5 cm

Butane 2b—6.5 cm

Butane 3—8.75

The study was performed over a 50 day period. During this period, tank temperature ranged from 66° lights off to 74° lights on. The fish were fed a diet of dried krill shrimp one or two times per day. Excess/uneaten food was removed immediately to prevent tank fouling. Tank bottoms were periodically cleaned of fish waste using a net. Water was tested for dissolved oxygen (DO) and ammonia using a Chemetrics photometer. Water was also tested for pH using a Chemetrics pH meter calibrated with 7.0 buffer solution. Water chemistry testing and replacement to offset high ammonia or pH was performed as recorded in Table 1.

TABLE 1

Water Chemistry Testing

| Day No. | Tank | Ammonia (ppm) | pH | DO (ppm) | Volume Water Changed |
| --- | --- | --- | --- | --- | --- |
| 3 | Control 1 | — | 6.3 | 8.0 | 600 ml |
| 3 | Control 2 | — | 6.3 | 8.0 | 600 ml |
| 3 | Butane 1 | — | 7.0 | 7.0 | 600 ml |
| 3 | Butane 2 | — | 7.0 | 7.0 | 600 ml |
| 3 | Butane 3 | — | 7.0 | 7.0 | 600 ml |
| 6 | Control 1 | 0.0 | 6.8 | 8.0 | — |
| 6 | Control 2 | 4.3 | 6.7 | 8.0 | 3000 ml |
| 6 | Butane 1 | 0.2 | 6.6 | 8.0 | — |
| 6 | Butane 2 | 6.2 | 7.0 | 8.0 | 3000 ml |
| 6 | Butane 3 | 5.7 | 7.0 | 8.0 | 3000 ml |
| 7 | Control 1 | 0.061 | — | — | — |
| 7 | Control 2 | 0.253 | — | — | — |
| 7 | Butane 1 | 0.106 | — | — | — |
| 7 | Butane 2 | 0.339 | — | — | — |
| 7 | Butane 3 | 0.409 | — | — | — |
| 8 | Control 1 | 0.065 | — | — | — |
| 8 | Control 2 | 0.222 | — | — | — |
| 8 | Butane 1 | 0.117 | — | — | — |
| 8 | Butane 2 | 0.336 | — | — | — |
| 8 | Butane 3 | 0.383 | — | — | — |
| 9 | Control 1 | 0.9 | 7.4 | 8.0 | 1900 ml |
| 9 | Control 2 | 4.1 | 7.3 | 8.0 | 1900 ml |
| 9 | Butane 1 | 2.4 | 7.2 | 8.0 | 1900 ml |
| 9 | Butane 2 | 6.4 | 7.3 | 8.0 | 190 ml |
| 9 | Butane 3 | 7.4 | 7.3 | 8.0 | 1900 ml |
| 10 | Control 1 | 1.1 | — | — | 3000 ml |
| 10 | Control 2 | 3.6 | — | — | 3000 ml |
| 10 | Butane 1 | 2.1 | — | — | 3000 ml |
| 10 | Butane 2 | 4.4 | — | — | 3000 ml |
| 10 | Butane 3 | 3.8 | — | — | 3000 ml |
| 11 | Control 1 | 0.3 | — | — | 3000 ml |
| 11 | Control 2 | 2.3 | — | — | 3000 ml |
| 11 | Butane 1 | 1.4 | — | — | 3000 ml |
| 11 | Butane 2 | 2. | — | — | 3000 ml |
| 11 | Butane 3 | 5.6 | — | — | 3000 ml |
| 12 | Control 1 | 1.1 | — | — | 3000 ml |
| 12 | Control 2 | 2.6 | — | — | 3000 ml |
| 12 | Butane 1 | 2.4 | — | — | 3000 ml |
| 12 | Butane 2 | 2.3 | — | — | 3000 ml |
| 12 | Butane 3 | 6.6 | — | — | 3000 ml |
| 13 | Control 1 | 0.9 | — | — | — |
| 13 | Control 2 | 1.0 | — | — | — |
| 13 | Butane 1 | 1.9 | — | — | — |
| 13 | Butane 2 | 0.9 | — | — | — |
| 13 | Butane 3 | 4.0 | — | — | 3000 ml |
| 14 | Control 1 | 1.1 | 7.6 | — | 3000 ml |
| 14 | Control 2 | 1.1 | 7.3 | — | — |
| 14 | Butane 1 | 3.1 | 7.2 | — | 3000 ml |
| 14 | Butane 2 | 1.6 | 7.1 | — | — |
| 14 | Butane 3 | 4.5 | 7.1 | — | 3000 ml |
| 16 | Control 1 | 0.8 | — | — | — |
| 16 | Control 2 | 0.0 | — | — | — |
| 16 | Butane 1 | 1.1 | — | — | 1500 ml |
| 16 | Butane 2 | 0.1 | — | — | — |
| 16 | Butane 3 | 3.2 | — | — | 3000 ml |
| 17 | Control 1 | 1.4 | — | — | 3000 ml |
| 17 | Control 2 | 0.4 | — | — | — |
| 17 | Butane 1 | 0.3 | — | — | — |
| 17 | Butane 2 | 0.3 | — | — | — |
| 17 | Butane 3 | 3.5 | — | — | 3000 ml |
| 19 | Control 1 | 0.0 | — | — | — |
| 19 | Control 2 | 0.0 | — | — | — |
| 19 | Butane 1 | 0.0 | — | — | — |
| 19 | Butane 2 | 0.2 | — | — | — |
| 19 | Butane 3 | 0.9 | — | — | — |
| 20 | Control 1 | 0.0 | — | — | — |
| 20 | Control 2 | 0.0 | — | — | — |
| 20 | Butane 1 | 0.0 | — | — | — |
| 20 | Butane 2 | 0.0 | — | — | — |
| 20 | Butane 3 | 0.6 | — | — | — |
| 21 | Control 1 | 0.0 | 8.8 | — | — |
| 21 | Control 2 | 0.0 | 8.5 | — | — |
| 21 | Butane 1 | 0.0 | 8.4 | — | — |
| 21 | Butane 2 | 0.0 | 8.7 | — | — |
| 21 | Butane 3 | 1.2 | 9.0 | — | 3000 ml |
| 22 | Control 1 | 0.0 | 8.7 | — | — |
| 22 | Control 2 | 0.1 | 8.1 | — | — |
| 22 | Butane 1 | 0.3 | 8.4 | — | — |
| 22 | Butane 2 | 0.0 | 8.1 | — | — |
| 22 | Butane 3 | 0.3 | 8.3 | — | — |
| 24 | Control 1 | 0.0 | 8.1 | 7.0 | — |
| 24 | Control 2 | 0.1 | 8.0 | 7.0 | — |
| 24 | Butane 1 | 0.2 | 8.0 | 6.9 | — |
| 24 | Butane 2 | 0.2 | 8.4 | 6.7 | — |
| 24 | Butane 3 | 0.2 | 9.1 | 6.5 | — |
| 27 | Control 1 | 0.0 | — | — | — |
| 27 | Control 2 | 0.0 | — | — | — |
| 27 | Butane 1 | 0.0 | — | — | — |
| 27 | Butane 2 | 0.0 | — | — | — |
| 27 | Butane 3 | 0.0 | — | — | — |
| 29 | Control 1 | 0.0 | — | — | — |
| 29 | Control 2 | 0.0 | — | — | — |

TABLE 1-continued

Water Chemistry Testing

| Day No. | Tank | Ammonia (ppm) | pH | DO (ppm) | Volume Water Changed |
|---|---|---|---|---|---|
| 29 | Butane 1 | 0.0 | — | — | — |
| 29 | Butane 2 | 0.0 | — | — | — |
| 29 | Butane 3 | 0.0 | — | — | — |
| 30 | Control 1 | 0.0 | 6.8 | — | — |
| 30 | Control 2 | 0.0 | 6.9 | — | — |
| 30 | Butane 1 | 0.0 | 6.8 | — | — |
| 30 | Butane 2 | 0.0 | 6.4 | — | — |
| 30 | Butane 3 | 0.1 | 6.6 | — | — |
| 34 | Control 1 | 0.0 | 7.1 | — | 1500 ml |
| 34 | Control 2 | 0.0 | 7.0 | — | 1500 ml |
| 34 | Butane 1 | 0.0 | 6.8 | — | 1500 ml |
| 34 | Butane 2 | 0.0 | 6.9 | — | 1500 ml |
| 34 | Butane 3 | 0.0 | 7.0 | — | 1500 ml |
| 35 | Control 1 | 0.0 | 7.0 | — | 1500 ml |
| 35 | Control 2 | 0.0 | 7.0 | — | 1500 ml |
| 35 | Butane 1 | 0.0 | 6.8 | — | 1500 ml |
| 35 | Butane 2 | 0.1 | 6.7 | — | 1500 ml |
| 35 | Butane 3 | 0.1 | 6.8 | — | 1500 ml |
| 36 | Control 1 | 0.0 | 6.9 | — | 1500 ml |
| 36 | Control 2 | 0.2 | 6.7 | — | 1500 ml |
| 36 | Butane 1 | 0.1 | 6.7 | — | 1500 ml |
| 36 | Butane 2 | 0.2 | 6.7 | — | 1500 ml |
| 36 | Butane 3 | 0.4 | 6.8 | — | 1500 ml |
| 37 | Control 1 | 0.0 | 6.4 | — | 1500 ml |
| 37 | Control 2 | 0.1 | 6.6 | — | 1500 ml |
| 37 | Butane 1 | 0.0 | 6.6 | — | 1500 ml |
| 37 | Butane 2 | 0.1 | 6.7 | — | 1500 ml |
| 37 | Butane 3 | 0.2 | 6.8 | — | 1500 ml |
| 38 | Control 1 | 0.3 | 6.7 | — | 1500 ml |
| 38 | Control 2 | 0.3 | 6.5 | — | 1500 ml |
| 38 | Butane 1 | 0.2 | 6.5 | — | 1500 ml |
| 38 | Butane 2 | 0.3 | 6.5 | — | 1500 ml |
| 38 | Butane 3 | 0.5 | 6.5 | — | 1500 ml |
| 39 | Control 1 | 0.0 | 6.8 | — | — |
| 39 | Control 2 | 0.0 | 6.6 | — | — |
| 39 | Butane 1 | 0.1 | 6.6 | — | — |
| 39 | Butane 2 | 0.2 | 6.5 | — | — |
| 39 | Butane 3 | 0.0 | 6.5 | — | — |
| 41 | Control 1 | 0.0 | 6.7 | — | — |
| 41 | Control 2 | 0.0 | 6.5 | — | — |
| 41 | Butane 1 | 0.0 | 6.5 | — | — |
| 41 | Butane 2 | 0.0 | 6.4 | — | — |
| 41 | Butane 3 | 0.0 | 6.5 | — | — |
| 43 | Control 1 | 0.0 | 6.7 | — | — |
| 43 | Control 2 | 0.6 | 6.3 | — | — |
| 43 | Butane 1 | 0.1 | 6.5 | — | — |
| 43 | Butane 2 | 0.0 | 6.3 | — | — |
| 43 | Butane 3 | 0.0 | 6.3 | — | — |
| 45 | Control 1 | 0.0 | 6.6 | — | — |
| 45 | Control 2 | 1.1 | 6.4 | — | 1500 ml |
| 45 | Butane 1 | 0.1 | 6.4 | — | — |
| 45 | Butane 2 | 0.9 | 6.2 | — | 1500 ml |
| 45 | Butane 3 | 0.5 | 6.3 | — | 1500 ml |
| 46 | Control 1 | 0.0 | 6.7 | — | — |
| 46 | Control 2 | 1.0 | 6.4 | — | 1500 ml |
| 46 | Butane 1 | 0.2 | 6.4 | — | — |
| 46 | Butane 2 | 0.7 | 6.4 | — | 1500 ml |
| 46 | Butane 3 | 0.4 | 6.4 | — | — |
| 48 | Control 1 | 0.0 | 6.9 | — | — |
| 48 | Control 2 | 0.1 | 6.8 | — | — |
| 48 | Butane 1 | 0.0 | 6.7 | — | — |
| 48 | Butane 2 | 0.0 | 6.7 | — | — |
| 48 | Butane 3 | 0.4 | 6.6 | — | — |
| 49 | Control 1 | 0.0 | 7.1 | — | — |
| 49 | Control 2 | 1.0 | 6.8 | — | 1500 ml |
| 49 | Butane 1 | 0.1 | 6.8 | — | — |
| 49 | Butane 2 | 0.2 | 6.6 | — | — |
| 49 | Butane 3 | 0.6 | 6.5 | — | — |
| 50 | Control 1 | 0.0 | 7.1 | — | — |
| 50 | Control 2 | 0.0 | 7.0 | — | — |
| 50 | Butane 1 | 0.0 | 6.8 | — | — |
| 50 | Butane 2 | 0.0 | 6.8 | — | — |
| 50 | Butane 3 | 0.6 | 6.8 | — | — |

Water was also tested periodically for carbon dioxide. Chemetrics titration tests consistently returned a result of ND.

During injections the removable injection tubing was placed in the tanks with the blue stone/sponge submerged to the tank bed. Butane (n-butane) was injected, without air, using a 50 ml gas-tight syringe into Butane Tanks 1, 2 and 3, as recorded in Table 2.

TABLE 2

Butane Injection Schedule (Butane 1, Butane 2, Butane 3)
(same volume injected in all three butane tanks unless otherwise noted)

| Day No. | Time | Volume of Butane |
|---|---|---|
| 3 | 13:40 | 50 ml |
| 4 | 10:47 | 50 ml |
| 5 | 13:30 | 50 ml |
| 6 | 09:00 | 50 ml |
| 7 | 18:00 | 50 ml |
| 8 | 16:10 | 75 ml |
| 9 | 09:36 | 100 ml |
| 10 | 17:20 | 100 ml |
| 11 | 16:30 | 100 ml |
| 12 | 14:30 | 150 ml |
| 13 | 13:11 | 150 ml |
| 14 | 13:30 | 150 ml |
| 15 | 17:10 | 150 ml |
| 16 | 17:55 | 150 ml |
| 17 | 20:06 | 150 ml |
| 18 | 17:53 | Butane 1 - 150 ml<br>Butane 2 - 200 ml<br>Butane 3 - 250 ml |
| 19 | 14:30 | Butane 1 - 150 ml<br>Butane 2 - 200 ml<br>Butane 3 - 250 ml |
| 20 | 11:15 | Butane 1 - 150 ml<br>Butane 2 - 200 ml<br>Butane 3 250 ml |
| 21 | 13:00 | Butane 1 - 150 ml<br>Butane 2 - 200 ml<br>Butane 3 250 ml |
| 22 | 10:05 | Butane 1 - 150 ml<br>Butane 2 - 200 ml<br>Butane 3 250 ml |
| 23 | 10:00 | Butane 1 - 150 ml<br>Butane 2 - 200 ml<br>Butane 3 250 ml |
| 24 | 12:37 | Butane 1 - 150 ml<br>Butane 2 - 200 ml<br>Butane 3 250 ml |
| 25 | 19:00 | Butane 1 - 150 ml<br>Butane 2 - 200 ml<br>Butane 3 - 250 ml |
| 26 | 14:30 | 200 ml |
| 27 | 09:26 | 200 ml |
| 28 | 14:30 | 200 ml |
| 29 | 11:20 | 200 ml |
| 30 | 11:30 | 200 ml |
| 31 | 14:00 | 200 ml |
| 32 | 15:30 | 200 ml |
| 33 | 12:30 | 200 ml |
| 34 | 16:39 | 200 ml |
| 35 | 09:30 | 200 ml |
| 36 | 10:28 | 200 ml |
| 37 | 18:30 | 200 ml |
| 38 | 17:10 | 200 ml |

TABLE 2-continued

Butane Injection Schedule (Butane 1, Butane 2, Butane 3)
(same volume injected in all three butane tanks unless otherwise noted)

| Day No. | Time | Volume of Butane |
| --- | --- | --- |
| 39 | 14:58 | 200 ml |
| 40 | 12:46 | 200 ml |
| 41 | 16:00 | 200 ml |
| 42 | 18:44 | 200 ml |
| 43 | 08:45 | 200 ml |
| 44 | 18:45 | 200 ml |
| 45 | 17:35 | 200 ml |
| 46 | 11:35 | 200 ml |
| 47 | 17:45 | 200 ml |
| 48 | 11:20 | 200 ml |
| 49 | 12:06 | 200 ml |
| 50 | 09:45 | 200 ml |
| 51 | — | — |

Day 3—Approximately 5 minutes following the first butane injection, all fish in Butane Tanks 1, 2, and 3 exhibited increased activity, short bursts of speed not observed in Control 1 or 2. The fish in control 1 and 2 were observed to sit near the bottom of the tank.

Day 4—Fish activity in Butane 1, 2 and 3 increased significantly immediately following butane injection. The fish again exhibited short bursts of speed/erratic movements. Two fish in Butane Tank 2 displayed aggressive behavior, bumping/nipping at each other. The fish in Butane 2 and 3 appeared to be rubbing their sides up against plant leaves and on the gravel bed. This behavior would normally be seen in fish infested with parasites. However, no parasites were ever observed in the tanks, free-swimming, on the tank walls, or in fish excrement. Since the behavior is sudden, it was attributed to the butane dosage just delivered. At the same time, fish in Control 1 and 2 were floating near the tank bottoms. Markings on fish in Butane Tanks 1, 2 and 3 also appeared to have darkened and become more distinct since the previous day.

Day 5—Following butane injection, fish in Butane 2 and 3 exhibited increased swimming activity. The fish in Butane 2 were bumping and nipping at each other. The fish in Butane 3 swam into the butane bubbles during injection, twitching and opening its mouth. New markings/spots have appeared on fish in Butane 1 and 3 since the previous day.

Day 6—Fish in Butane 1, 2 and 3 exhibited increased swimming activity post

Day 7—Fish in Butane 2 displayed increased swimming/aggressive behavior during and following butane injection. Fish in Butane 3 waited at bottom next to blue butane injection stone and stayed near stone during injection opening mouth wide, but did not appear to be agitated.

Day 8—Fish in Butane 3 swam into bubbles during injection.

After one week, increased swimming and aggressive behavior (two fish in Butane 2) following butane injection diminished in all fish. All Butane fish swim through bubbles during injection. Fish in Butane 3 repeatedly follows blue injection stone/sponge to bottom upon insertion and appeared to wait for the butane bubbles. Fish in Butane Tanks 1, 2 and 3 began to display increased hunger, regularly eating more pieces of krill than fish in Control Tanks 1 and 2. Fish seem to be watching as person entered room, waited at surface and snapped at food as soon as it is held over the water. After eating, all fish settled to the tank bottoms and appeared calm. It also appeared that butane may have an almost "narcotic" effect on fish. They apparently became accustomed to the injections, no longer becoming agitated post butane injection after one week.

After two weeks, plants in Control Tanks 1 and 2 each exhibited at least one totally burned (ammonia) and at least one other partially burned leaf. No burned or dead leaves developed in Butane 1, 2 or 3. Control Tank 1 showed no algae at two weeks. Control Tank 2 showed a few small spots of green, bluegreen or red/brown algae on two leaves. The plant in Butane 1 had four leaves mostly covered with several spots of green/bluegreen algae and large patches of red/brown algae. The Butane 2 plant had five leaves mostly covered with red/brown, blue and bluegreen algae. Butane 3 plant had one leaf covered with red/brown algae and three other leaves with several spots of green/bluegreen algae.

Figure 2A:
FIGS. 2a, 2b and 2c are pictorial representations of experimental tank setups. The two upper photographs show control fish tanks. The lower photograph shows a butane-enhanced fish tank.
Figure 2B:
Figure 2C:

By the end of the 50 day period, there was significantly more algae on plant leaves, tank walls and air filter tubing in Butane 1, 2 and 3 as compared to Control 1 and 2, as shown in FIG. 2. Control 1 and 2 plants both lost two leaves, whereas Butane 1, 2 and 3 plants appeared to be very healthy, no leaves lost and no burned spots. The water in Butane 1, 2 and 3 also had a significantly more turbid appearance and thicker consistency with more particle matter floating throughout. The water had a soupy quality, most significantly in Butane 1.

Figure 3:
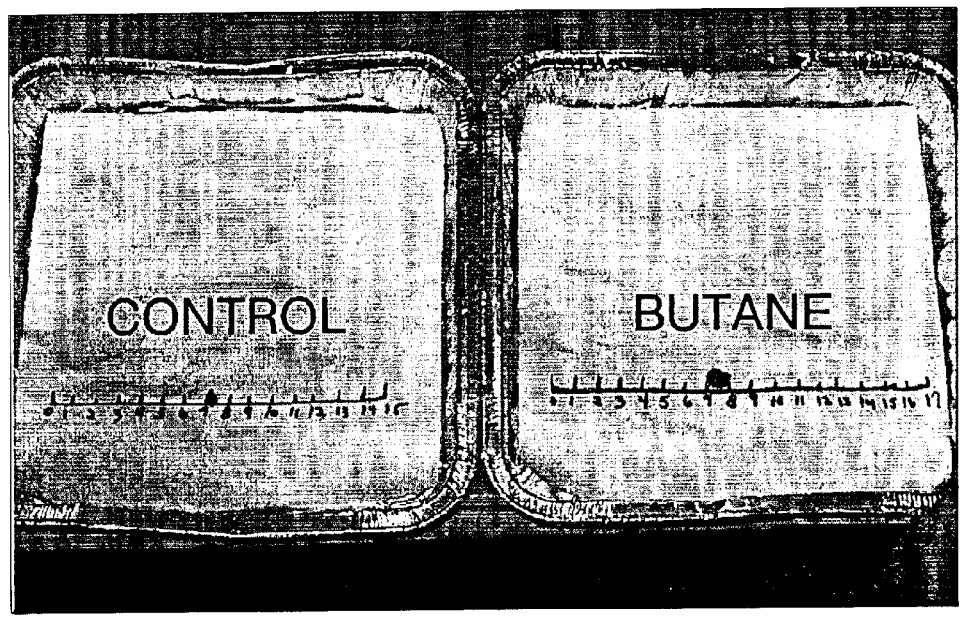
FIG. 3 is a pictorial representation illustrating a small snail grown in a control fish tank versus a large snail which exhibited accelerated growth in a butane-enhanced tank.

Tiny snails were first observed on Day 18 in Control 2 and Butane 2 (probably brought in on plants). These snails were observed throughout the rest of the experiment period cleaning algae from leaves, tank sides, gravel and air filter tubes (both above and beneath water surface). When first sighted, the snail in Butane 2 was approximately 1.5 times the size of the snail in Control 2. By the end of the 50 day period, the snail in Butane 2 was at least four times the size of the snail in Control 2, as shown in FIG. 3. This may be a result of a significantly more abundant food/algae supply available in Butane 2.

Figure 4:
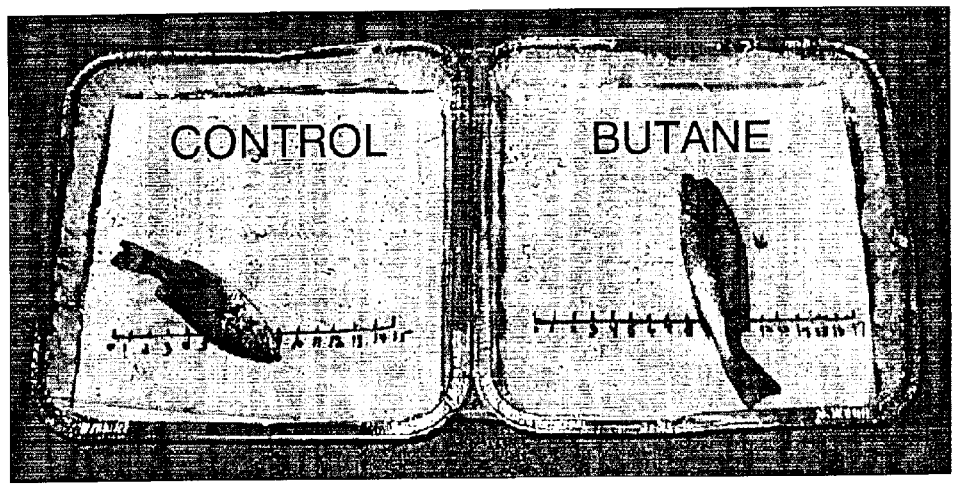
FIG. 4 is a pictorial representation illustrating a relatively small fish grown in a control tank in comparison with a relatively large fish exhibiting accelerated growth in a butane-enhanced tank.
Figure 5:
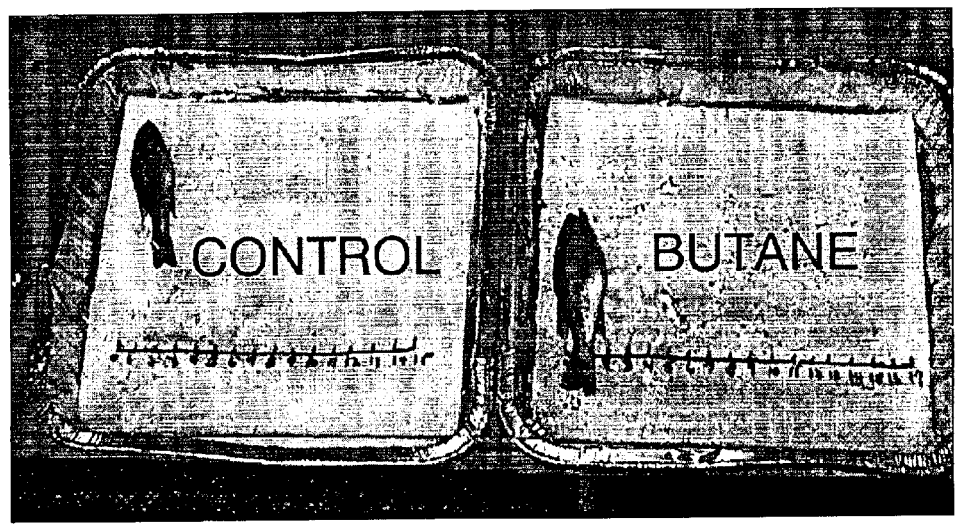
FIG. 5 is a pictorial representation illustrating a relatively small fish grown in a control tank in comparison with a relatively large fish exhibiting accelerated growth in a butane-enhanced tank.

At the end of the 50 day period the fish in Butane 1 was the largest and was significantly larger in length and girth than the fish in Control 2, which had been the same size at the beginning of the experiment, as shown in FIG. 4. The fish in Butane 2a, which was initially close in size to Control 1, had also increased by a larger percentage as compared to Control 1, as shown in FIG. 5. The growth changes over the 50 day period for all fish are recorded in Table 3.

TABLE 3

| | Length Only Measurements | | |
| --- | --- | --- | --- |
| Identification | Length Day 1 | Length Day 50 | % Increase |
| Control 1 | 6.0 | 8.0 | 33% |
| Control 2 | 7.5 | 12.0 | 60% |
| Butane 1 | 7.5 | 13.0 | 73% |
| Butane 2a | 6.5 | 9.0 | 38% |
| Butane 2b | 6.5 | 9.0 | 38% |
| Butane 3 | 8.75 | 13.0 | 48.5% |

The fish had been removed from their tanks to have their lengths measured. Post measurement fish appeared stressed by the process, so exact girth measurement was not attempted. All of the fish in Butane 1, 2 and 3 were observed to be significantly "fatter", i.e. larger in girth than the Control 1 and 2 fish. This substantial increase of the butane fish in terms of girth is likely a direct result of their increased hunger and resulting increase in food consumption post butane injection as compared to the control fish.

On Day 15, a 150 ml water sample from Butane 1 was analyzed for butane 30 minutes post butane injection using a SRI Instruments Gas Chromatograph (GC) equipped with a flame ionization detector (FID). The GC was calibrated using external standards. The results yielded a concentration of 10 milligrams per liter (ppm).

Figure 6:
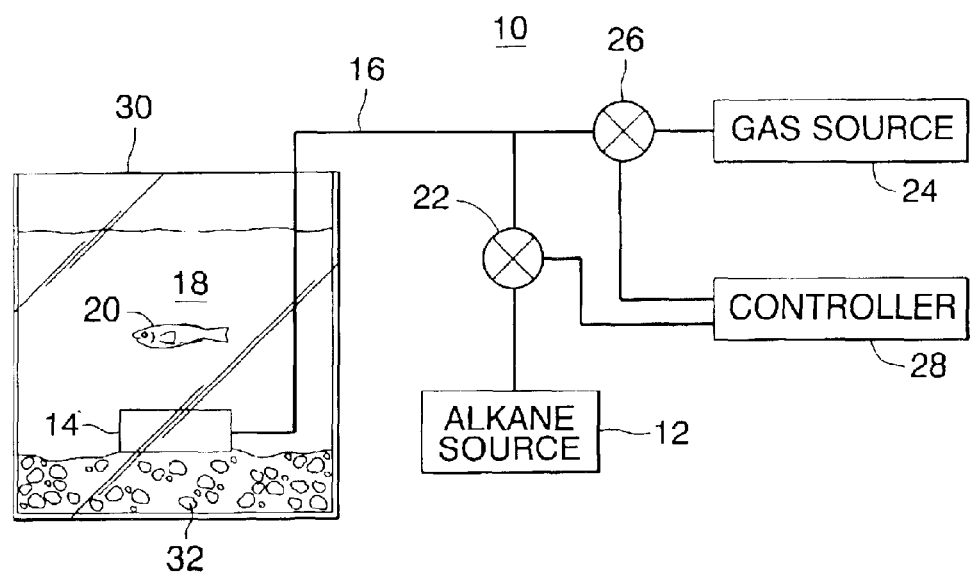
FIG. 6 is a schematic representation of a system for enhancing aquatic organism growth constructed in accordance with the invention.

FIG. 6 is a schematic representation of a system 10 for enhancing aquatic organism growth constructed in accordance with the invention. The system includes an alkane source 12 connected to an injector 14 by a tube 16. The injector is positioned in water 18 containing at least one aquatic organism 20. A valve 22 can be included to control the flow of the alkane. Another gas source 24, such as an air pump, can also be connected to the tube 16 through a valve 26. A controller 28 can be used to control the operation of the valves. In the illustrated embodiment, the water is contained in a container 30 and a layer of gravel 32 is provided at the bottom of the container. The alkane source can be a tank of alkane, such as butane or a butane substrate, or a syringe of butane or a butane substrate.

The alkane may be injected, for example, through existing piping networks that deliver nutrients and chemicals to the water reservoirs. The alkane may be injected alone, simultaneously or intermittently with other nutrients or chemicals. The alkane may also be injected simultaneously or intermittently with air or other gases.

For aerobic treatment, an oxygen-containing gas may also be introduced into the water. The introduction of oxygen-containing gas may be accomplished by any suitable means such as injection tubes for introducing the gas alone or in a carrier fluid, or by exposing the water to the atmosphere.

The alkane can be supplied from an alkane source such as alkane cylinder and can be delivered to the water reservoir using one or more injectors, with an end or other portion of the injectors extending into the desired location. The alkane source can be connected to the injectors through one or more pipes or tubes. The alkane can be injected with a pusher gas, such as helium. One or more valves can be used between the alkane source, a pusher gas source, and the injectors to control the flow of the alkane and the pusher gas. A controller can be provided to control the valve, and the controller can include a timer that controls the timing of operation of the valve. The alkane can be supplied in gaseous or liquid form. Various forms of injectors can be used, including injectors having a proximal for receiving the alkane and a distal end for dispersing the alkane. The distal end can include a plurality of openings.

In one embodiment of the invention, the alkane is butane or a butane substrate, but other compounds can be used such as methane, ethane, propane or any higher order alkane. As used herein, the term butane substrate includes liquids and gases in which butane is present in sufficient amounts to stimulate substantial growth of butane-utilizing bacteria. Butane is preferably the most prevalent compound of the butane substrate on a weight percent basis, and typically comprises at least about 10 weight percent of the butane substrate. The other constituents of the butane substrate may include other hydrocarbon compounds, such as other alkanes, i.e., methane, ethane and propane. The butane substrate preferably comprises at least about 50 weight percent butane. More preferably, the butane substrate comprises at least about 90 weight percent butane. In a particular embodiment, the butane substrate comprises at least about 99 weight percent n-butane. The butane may contain straight (n-butane) and/or branched chain compounds such as iso-butane.

Butane is highly soluble and ideally suited to serve as a growth substrate. The butane may be injected intermittently or substantially continually.

Whereas particular embodiments of this invention have been described above for purposes of illustration, it will be evident to those skilled in the art that numerous variations of the details of the present invention may be made without departing from the invention.

What is claimed is:

1. A method of enhancing aquatic organism growth comprising the step of:
   introducing an alkane comprising at least about 10 weight percent butane, propane and/or ethane into water containing the organism to enhance growth of the organism during the introduction of the alkane, wherein the organism comprises a fish, crustacean, mollusk, algae or aquatic plant.

2. The method of claim 1, wherein the alkane is introduced intermittently.

3. The method of claim 1, further comprising the step of: introducing another gas with the alkane.

4. The method of claim 3, wherein the other gas comprises an oxygen containing gas.

5. The method of claim 1, further comprising the step of: introducing nutrients with the alkane.

6. The method of claim 1, wherein the alkane comprises a butane substrate.

7. The method of claim 6, wherein the butane substrate comprises at least about 10 weight percent butane.

8. The method of claim 6, wherein the butane substrate comprises at least about 50 weight percent butane.

9. The method of claim 6, wherein the butane substrate comprises at least about 90 weight percent butane.

10. The method of claim 6, wherein the butane substrate comprises at least about 99 weight percent n-butane.

11. The method of claim 6, wherein the butane substrate comprises at least one of n-butane and iso-butane.

12. The method of claim 6, wherein butane is the most prevalent compound of the butane substrate on a weight percent basis.

13. The method of claim 1, wherein the alkane is introduced into the water by injecting the alkane into the water.

14. The method of claim 13, wherein the alkane is injected into the water from an alkane source external to the water.

15. The method of claim 1, wherein the alkane is introduced to the water under pressure.

16. An organism grown by the method of claim 1.

17. A system for enhancing aquatic organism growth comprising:
   means for introducing an alkane comprising at least about 10 weight percent butane, propane and/or ethane into water containing the organism to enhance growth of the organism during the introduction of the alkane, wherein the organism comprises a fish, crustacean, mollusk, algae or aquatic plant.

18. The system of claim 17, wherein the alkane is introduced intermittently.

19. The system of claim 17, wherein another gas is introduced with the alkane.

20. The system of claim 19, wherein the other gas comprises an oxygen containing gas.

21. The system of claim 17, wherein nutrients are introduced with the alkane.

22. The system of claim 17, wherein the alkane comprises a butane substrate.

23. The system of claim 22, wherein the butane substrate comprises at least about 10 weight percent butane.

24. The system of claim 22, wherein the butane substrate comprises at least about 50 weight percent butane.

25. The system of claim 22, wherein the butane substrate comprises at least about 90 weight percent butane.

26. The system of claim 22, wherein the butane substrate comprises at least about 99 weight percent n-butane.

27. The system of claim 22, wherein the butane substrate comprises at least one of n-butane and iso-butane.

28. The system of claim 22, wherein butane is the most prevalent compound of the butane substrate on a weight percent basis.

29. The system of claim 22, wherein the means for introducing an alkane comprises:

at least one injector in flow communication with an alkane source, wherein at least a portion of the injector is positioned in the water.

30. The system of claim 29, wherein the alkane source comprises a butane cylinder.

31. The system of claim 30, wherein the butane cylinder is in flow communication with a source of pusher gas.

32. The system of claim 29, wherein the alkane source comprises means for storing the butane substrate in liquid form.

33. The system of claim 29, wherein the butane substrate is supplied to the injector in liquid form.

34. The system of claim 29, wherein the alkane is supplied to the injector in gaseous form.

35. The system of claim 29, further comprising at least one valve in flow communication between the alkane source and the at least one injector.

36. The system of claim 35, wherein the valve is in flow communication between a source of oxygen-containing gas and the at least one injector.

37. The system of claim 35, further comprising a controller for the at least one valve.

38. The system of claim 37, wherein the controller comprises means for periodically opening and closing the at least one valve.

39. The system of claim 37, wherein the controller comprises a timer.

* * * * *